(12) United States Patent
   Ray

(10) Patent No.: US 12,564,571 B2
(45) Date of Patent: Mar. 3, 2026

(54) COMPOSITIONS AND METHODS FOR THE TREATMENT OF EQUINE PROTOZOAL MYELOENCEPHALITIS

(71) Applicant: Going Big Time, Inc., Ada, OK (US)

(72) Inventor: Danny Ray, Ada, OK (US)

( * ) Notice: Subject to any disclaimer, the term of this patent is extended or adjusted under 35 U.S.C. 154(b) by 2043 days.

(21) Appl. No.: 16/280,877

(22) Filed: Feb. 20, 2019

(65) Prior Publication Data

US 2019/0255016 A1 Aug. 22, 2019

Related U.S. Application Data

(60) Provisional application No. 62/632,802, filed on Feb. 20, 2018.

(51) Int. Cl.
| | |
|---|---|
| *A61K 31/53* | (2006.01) |
| *A61K 9/16* | (2006.01) |
| *A61K 31/355* | (2006.01) |
| *A61K 31/425* | (2006.01) |
| *A61K 31/47* | (2006.01) |
| *A61K 31/675* | (2006.01) |
| *A61K 36/00* | (2006.01) |
| *A61K 36/68* | (2006.01) |
| *A61P 33/02* | (2006.01) |

(52) U.S. Cl.
   CPC .............. *A61K 31/355* (2013.01); *A61K 9/16* (2013.01); *A61K 31/425* (2013.01); *A61K 31/53* (2013.01); *A61K 31/675* (2013.01); *A61K 36/68* (2013.01); *A61P 33/02* (2018.01)

(58) Field of Classification Search
   CPC ...... A61K 31/53; A61K 31/47; A61K 31/355; A61K 31/458; A61K 36/00; A61K 36/68

USPC ........ 514/242, 312, 368, 458; 424/726, 738, 424/769
   See application file for complete search history.

(56) References Cited

U.S. PATENT DOCUMENTS

| | | | | |
|---|---|---|---|---|
| 5,747,476 | A | * | 5/1998 | Russell .................. A61K 31/63 |
| | | | | 514/275 |
| 5,830,893 | A | | 11/1998 | Russell |
| 5,883,095 | A | * | 3/1999 | Granstrom ............. A61K 31/53 |
| | | | | 514/241 |
| 5,935,591 | A | * | 8/1999 | Rossignol ............ A61K 31/425 |
| | | | | 424/405 |
| 6,465,460 | B1 | | 10/2002 | Hundley et al. |
| 2006/0240049 | A1 | | 10/2006 | De Spiegeleer et al. |
| 2014/0045885 | A1 | | 2/2014 | Ellison |
| 2015/0338394 | A1 | * | 11/2015 | Killeen .............. G01N 33/5088 |
| | | | | 800/8 |

FOREIGN PATENT DOCUMENTS

| | | |
|---|---|---|
| WO | WO 98/43644 | 10/1998 |

* cited by examiner

*Primary Examiner* — Raymond J Henley, III
(74) *Attorney, Agent, or Firm* — Michael F. Krieger

(57) ABSTRACT

Embodiments of the invention relate to veterinary compositions and methods for the treatment of Equine Protozoal Myeloencephalitis. Specifically, embodiments of the present invention feature methods and compositions designed to treat horses with EPM by killing the protozoan parasites in the horse's body and by providing agents that limit or remedy the damage caused by the protozoan parasites. In particular embodiments, therapeutically effective amounts of Vitamin E Succinate 1185 IU, Levamisole Hydrochloride, Decoquinate, Diclazuril, and Banana powder are administered to the horse for the treatment of Equine Protozoal Myeloencephalitis.

11 Claims, 2 Drawing Sheets

COMPOSITIONS AND METHODS FOR THE TREATMENT OF EQUINE PROTOZOAL MYELOENCEPHALITIS

CROSS-REFERENCE TO RELATED APPLICATIONS

The application claims priority benefit to U.S. Provisional Patent Application No. 62/632,802 filed Feb. 20, 2018 and titled "Compositions and Methods for the Treatment of Equine Protozoal Myeloencephalitis.

FIELD OF THE INVENTION

Embodiments of the present invention relate generally to the treatment of Equine Protozoal Myeloencephalitis in horses. In particular, embodiments of the invention relate to a horse feed comprising: Vitamin E Succinate, Levamisole Hydrochloride, Decoquinate, Diclazuril, and Banana powder for the effective treatment of Equine Protozoal Myeloencephalitis.

BACKGROUND OF THE INVENTION

Equine Protozoal Myeloencephalitis (EPM) is a progressive and degenerative neurologic disease that affects the central nervous system of horses. The most common cause of EPM is the one-celled protozoan parasite known as *Sarcocystis neurona*. However, recent investigations have indicated that EPM—in rare cases—may also be caused by the *Neospora caninum* and/or the *Neospora hughesi* protozoan parasites.

The *Sarcocystis neurona* parasite is generally thought to be carried by opossums, which serve as its definitive host. The parasite is spread when an infected opossum excretes sporocysts containing the parasite in their feces. The sporocysts are then ingested by an intermediate hosts—such as cats, armadillos, skunks and raccoons—where the parasite emerges from the sporocysts and travels to the muscle tissue of the intermediate host. When the intermediate host is eaten by an opossum, the cycle is completed.

Horses are considered an aberrant or dead-end host of the protozoan parasites. As a dead-end host, the infectious forms of the parasite are not passed from horse to horse. Accordingly, horses are presumably infected by ingesting feed, grass, or water contaminated with feces containing the protozoan parasites. It is estimated that more than 50 percent of all horses in the United States may have been exposed to the sporocysts containing protozoan parasites. As a result, a horse of any age, breed or sex may develop the EPM disease.

After a horse has ingested the sporocysts, the parasite travels through the digestive tract and enters the bloodstream. The parasite is then carried through the bloodstream where were it may cross the blood brain barrier if the parasite is not killed by the immune system. If the parasite crosses the blood brain barrier, it lives within the cell of the central nervous system, where it evades the horse's immune system and begins to reproduce. The reproduction process causes the host cell to die, which in turn causes inflammation, swelling, and lesions in the horse's brain, brain stem, and/or spinal cord. These lesions slowly impede that transmission of electrical signals from the brain.

Detecting the early onset of the EPM can be particularly difficult because the initial symptoms—including an abnormal gait or lameness—are common for a variety of health problems affecting horses. However, the condition becomes apparent when the horse begins to show signs of incoordination, stiff movements, poor balance, difficulty swallowing, loss of sensation, and even paralysis. If left untreated, EPM causes devastating and irreversible neurological damage to the horse.

Several medications have been developed to treat EPM. Generally, these drugs comprise an antiprotozoal agent that kills the parasite, or inhibits its growth and reproduction. However, these medications are not without their drawbacks. Notably, if the treatment is ended before all the parasites have been killed, an affected horse may have an EPM relapse. Moreover, known treatments focus on killing the parasites and not remedying the damage caused by the parasites. As a result, there remains an unfulfilled need for an EPM treatment that is effective, convenient, cost effective, and beneficial to the horse's recovery from EPM.

SUMMARY OF THE INVENTION

Some embodiments relate to formulations designed to prevent or control the EPM disease. Some embodiments relate to formulations that provide a specific health benefit to horses. Some embodiments are formulated to treat the EPM causing protozoan parasites in horses, and to mitigate or remedy the damage caused by the protozoan parasites. Some embodiments comprise an antiprotozoal agent, immunostimulant, an antioxidant agent, and banana powder.

Some embodiments provide an antiprotozoal agent selected from Diclazuril and Decoquinate. Some embodiments comprise a combination or two or more antiprotozoal agents. Some embodiments provide Levamisole Hydrochloride to elicit or amplify a horse's immune response. Some embodiments provide Vitamin E Succinate as an antioxidant agent. Some embodiments provide a high-fiber banana powder.

In some embodiment, the formulation is designed to be administered to a horse as a treatment regimen. In some embodiments, the formulation is administered to the horse as top-dressing to the horse's feed. In some embodiments, the formulation is administered to the horse orally. In some embodiments, the formulation is administered in liquid form. In some embodiments, the formulation is administered in paste form. In some embodiments, the formulation is administered in a pellet form. In some embodiments, the formulation is administered in several solid forms.

Preferred embodiments may be formulated to comprise: Vitamin E Succinate (or other forms of Vitamin E appropriate for the processing to achieve the ultimate form such as pellets), Levamisole Hydrochloride, Decoquinate, Diclazuril, and banana powder. In preferred embodiments, the regimen may require the administration of the formulation once a day, for thirty days.

BRIEF DESCRIPTION OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

It will be readily understood that the components of the present invention, as generally described herein, could be arranged and designed in a wide variety of different configurations. Thus, the following more detailed description of embodiments of the compositions and methods of the present invention is not intended to limit the scope of the invention, as claimed, but is merely representative of the presently preferred embodiments of the invention. Moreover, the following disclosure of the present invention may be grouped into subheadings. The utilization of the subheadings is for convenience of the reader only and is not to be construed as limiting in any sense. The scope of the invention is, therefore, indicated by the appended claims rather than by the foregoing description. All changes that come within the meaning and range of equivalency of the claims are to be embraced within their scope.

Embodiments of the present invention feature compositions and methods designed to treat horses with EPM by killing the protozoan parasites in the horse's body and by providing agents that limit or remedy the damage caused by the protozoan parasites. The general health benefit of the methods and compositions stem from the synergistic combination of treating the protozoan infection and providing the horse with agents that facilitate recovery.

Figure 1:
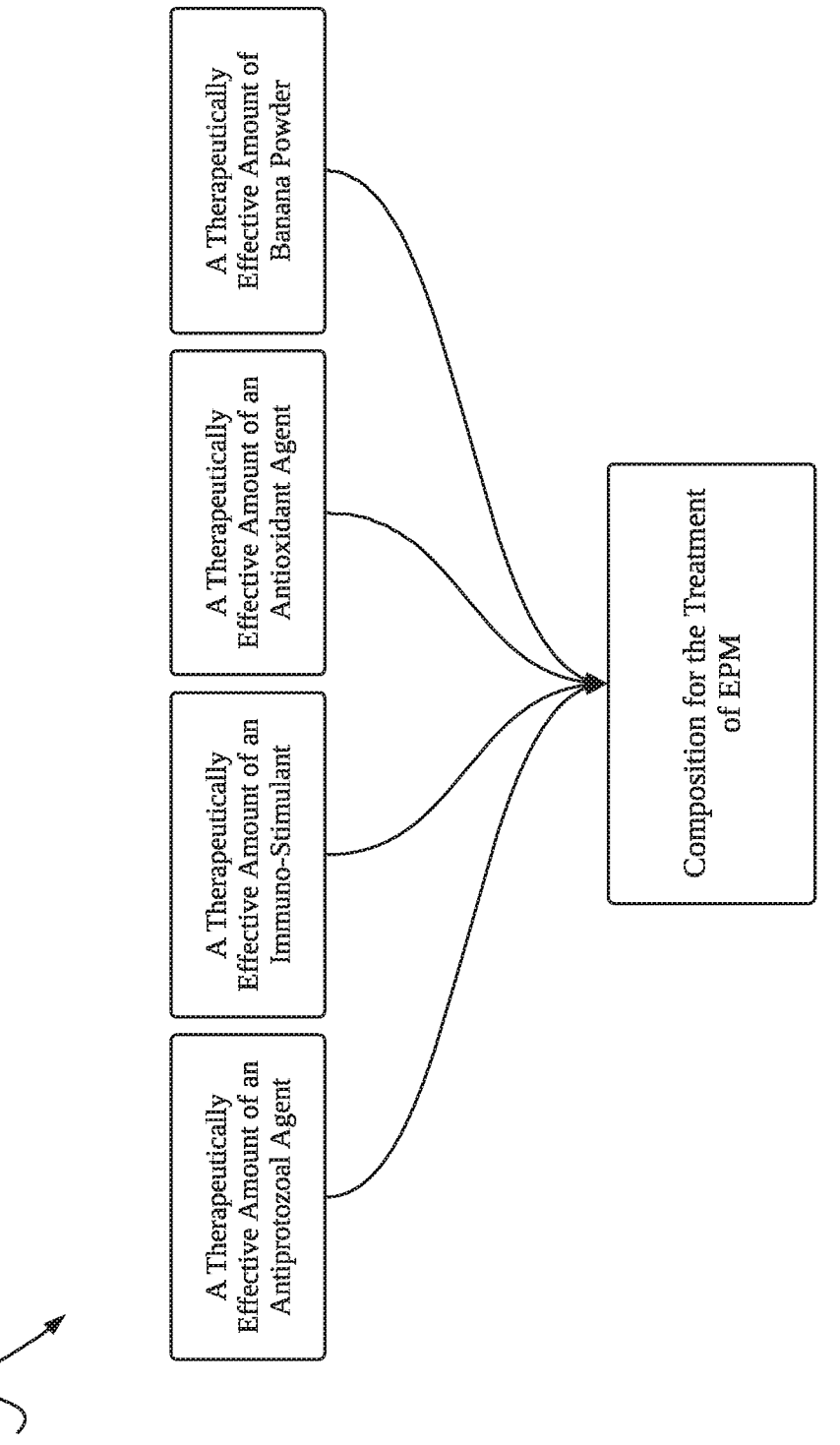
FIG. 1 depicts one embodying formulation of the veterinary composition for the treatment of Equine Protozoal Myeloencephalitis.

Embodiments of the present invention may comprise an antiprotozoal agent, an immuno-stimulant, an antioxidant agent, and banana powder. As depicted in FIG. 1, embodiments of the present invention may be formulated 12 by providing a therapeutically effective amount of an antiprotozoal agent, an immuno-stimulant, an antioxidant agent, and banana powder.

Antiprotozoal Agents:

In some embodiments, the composition may include one or more suitable antiprotozoal agents. Antiprotozoal agents are drugs that treat infections caused by protozoa parasites. The actions of antiprotozoal drugs are complex and are not fully understood. Generally, the antiprotozoal may treat the protozoa parasite by destroying the protozoa or inhibits its growth and ability to reproduce. Specifically, it is believed that some may interfere with reproduction of or damage protozoal DNA to limit the spread of an infection.

In some embodiments, an antiprotozoal agent may be selected based on its ability to treat a specific type of protozoa parasite. In some embodiments, an antiprotozoal agent may be selected based on its effectiveness in treating the *Sarcocystis neurona* parasite. In other embodiments, an antiprotozoal agent may be selected based on its effectiveness in treating the *Neospora hughesi* parasite. In yet other embodiments, an antiprotozoal agent may be selected based on its effectiveness in treating the *Neospora caninum* parasite.

In some embodiments, the antiprotozoal agent may be selected to treat the protozoa parasite at various points in the pathogenesis of the EPM disease. In some embodiments, the antiprotozoal agent may target the protozoa parasite in the intestines of the horse. In other embodiments, the antiprotozoal agent may target the protozoa parasite in the bloodstream of the horse. In yet other embodiments, the antiprotozoal agent may target the protozoa parasite in the central nervous system of the horse. In some embodiments, the composition may include two or more antiprotozoal agent, each targeting a different point in the pathogenesis of the EPM disease.

Figure 2:
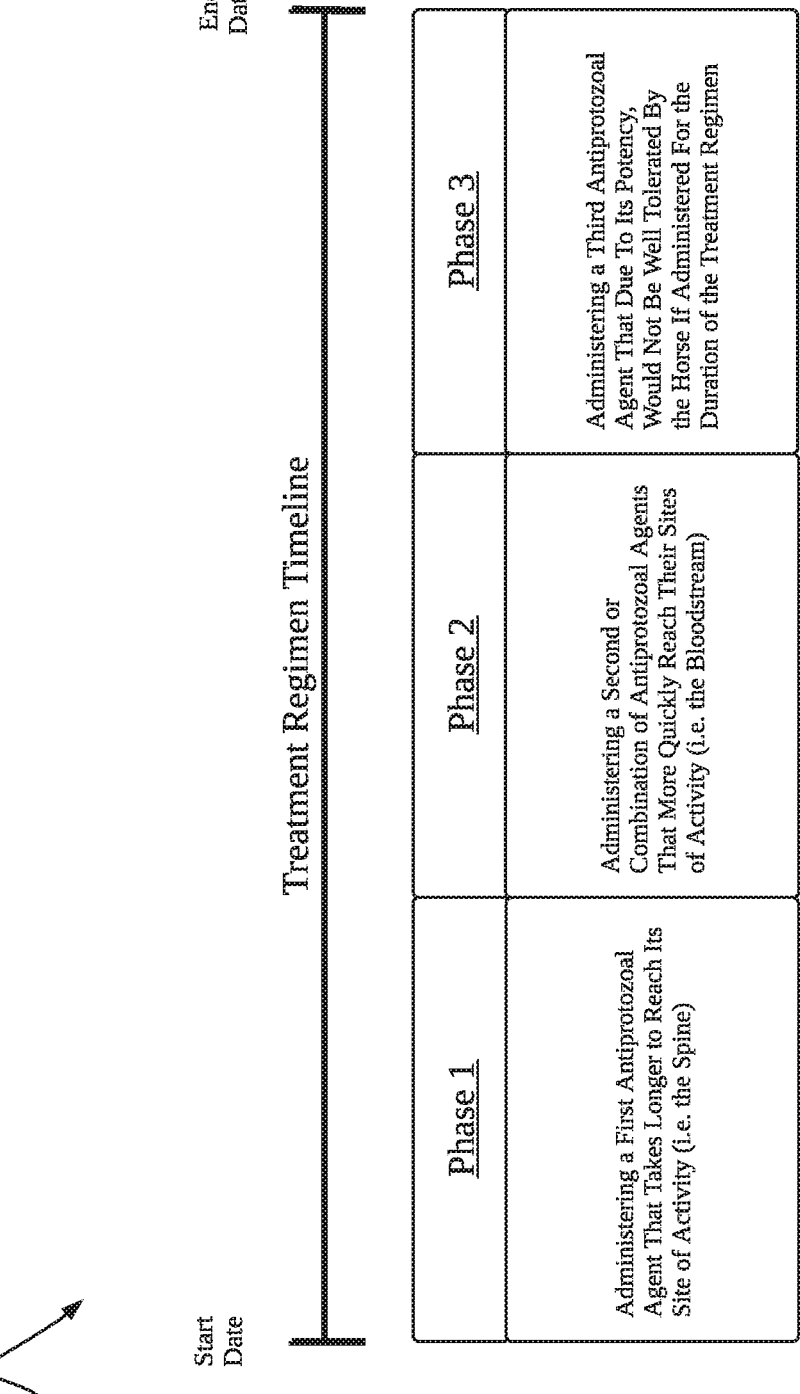
FIG. 2 depicts an embodying regimen for the administration of an embodying composition for the treatment of Equine Protozoal Myeloencephalitis, wherein the selected anti-protozoal agent changes during the duration of the regimen.

In some embodiments, an antiprotozoal agent may be selected from widely known antiprotozoal drugs, including: Allopurinol, Atovaquone, Azithromycin, Clindamycin, Decoquinate, Diclazuril, Diminazene Aceturate, Fenbendazole, Halofuginone, Imidocarb Dipropionate, Imidocarb, Imidocarb, Metronidazole, Ponazuril, and combinations thereof. In preferred embodiments, the composition may include the antiprotozoal agents Decoquinate and Diclazuril. As depicted in FIG. 2, the selection of antiprotozoal drugs 14 may change during the 30 day regimen so that the protozoa may be attacked at different sites at the same time. For example, drugs may be introduced in the first days of the regimen that take longer to reach their site of activity such as the spine, whereas other drugs attacking the protozoa through the bloodstream or in the intestines could be introduced through the formula during the later days in the regimen. Additionally, the quantity of antiprotozoal drug may vary throughout the regimen with higher quantities being included in the formulation near the end of the regimen when the horse will not need to tolerate it for a long period and when the protozoa may be at its weakest.

In some embodiments, an antiprotozoal agent may be selected based on its purity. In some embodiments, the purity may by measured by weight. In other embodiments, the purity may be measure by volume. In some embodiments, the purity of the antiprotozoal agent may range from 1 to 100 percent. In preferred embodiments, the antiprotozoal agent may range from 95 to 100 percent. In some embodiments, an antiprotozoal agent may be in liquid form. In other embodiments, an antiprotozoal agent may be in solid or powder form.

Immuno-Stimulants:

In some embodiments, the composition may include one or more immune-stimulants. Immuno-stimulants may be designed to elicit or amplify an immune response. Immuno-stimulants may aid in the clearance of persistent protozoa parasites in the horse's body. An immuno-stimulant may be characterized by the induction of macrophage activity and cytokine synthesis. Specifically, immuno-stimulants may act primarily by activating macrophages or other antigen presenting cells such as B lymphocytes or dendritic cells— enhancing the horse's natural defense to the protozoa parasites causing EPM.

In some embodiments, the immuno-stimulant may be selected based on its ability to boost the function of T lymphocytes in the immune system of a horse, especially when the immune system has been compromised by EPM. In preferred embodiments, the immuno-stimulant is Levamisole Hydrochloride.

In some embodiments, an immuno-stimulant may be selected based on its purity. In some embodiments, the purity may by measured by weight. In other embodiments, the purity may be measure by volume. In some embodiments, the purity of an immuno-stimulant may range from 1 to 100 percent. In preferred embodiments, the purity of an immuno-stimulant may range from 95 to 100 percent. In some embodiments, an immuno-stimulant may be in liquid form. In other embodiments, the immuno-stimulant may be in solid or powder form.

Antioxidant Agents:

In some embodiments, the composition may include one or more antioxidant agents. An antioxidant agent inhibits the oxidation of other molecules. The oxidation process may produce free radicals that damage cells. In some embodiments, the antioxidant may be selected based on ability to improve the horse's health. In other embodiments, the antioxidant may be selected based on its effectiveness in allowing the horse to recover from the damage caused by EPM parasites. In some embodiments, the antioxidant may be selected to ensure proper function of the horse's muscular, nervous, circulatory, or immune systems. In some embodiments, the antioxidant agent is a vitamin. In some embodiments, the antioxidant may be selected from Vitamin A, Vitamin C, Vitamin E, or combinations thereof. In preferred embodiments, the antioxidant agent may be Vitamin E. In some embodiments, the Vitamin E may be Vitamin E Succinate 1185 IU powder. In other embodiments, the Vitamin E may be Vitamin E Succinate 1210 IU powder.

In some embodiments, the antioxidant agent may be in liquid form. In other embodiments, the antioxidant agent may be in solid (such as pellets) or powder form (such as a top dressing).

Banana Powder:

In some embodiments, the composition may include banana powder or fenugreek powder. In some embodiments, the banana powder may be a fiber-rich banana powder. In some embodiments, the banana powder may be selected based on its fiber content. In other embodiments, the banana powder may be selected based on its oil and water holding capacity.

In some embodiments, the banana powder or fenugreek powder may be dissolved in liquid. In other embodiments, the banana powder may be in solid or powder form.

Additional Nutritional Ingredients:

In some embodiments, the composition may include additional nutritional ingredients for the effective treatment of EPM. Typical nutritional ingredients may include vitamins, minerals, trace elements, herbs, botanical extracts, bioactive chemicals, and compounds at concentrations from 0 to 20 percent by mass of the composition. Examples of vitamins include, but are not limited to, vitamins A, B1 through B12, C, D, E, Folic Acid, Pantothenic Acid, Biotin, etc. Examples of minerals and trace elements include, but are not limited to, calcium, chromium, copper, cobalt, boron, magnesium, iron, selenium, manganese, molybdenum, potassium, iodine, zinc, phosphorus, etc. Herbs and botanical extracts may include, but are not limited to, alfalfa grass, bee pollen, chlorella powder, Dong Quai powder, Echinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

In some embodiments, the additional nutritional ingredients may be in liquid form. In other embodiments, the additional nutritional ingredients may be in solid or powder form.

Formulations:

The following compositions or formulations represent some of the preferred embodiments contemplated by the present invention. However, these compositions are only intended to be exemplary, as one ordinarily skilled in the art will recognize other formulations or compositions comprising the processed product.

A composition of the present invention may comprise one or more antiprotozoal agents present in an amount by mass between about 0.01 and 100 percent by mass, and preferably between 5 and 35 percent by mass.

A composition of the present invention may comprise one or more immuno-stimulants present in an amount by mass between about 0.01 and 100 percent by mass, and preferably between 5 and 35 percent by mass.

A composition of the present invention may comprise one or more antioxidant agents present in an amount by mass between about 0.01 and 100 percent by mass, and preferably between 35 and 75 percent by mass.

A composition of the present invention may comprise banana powder present in an amount by mass between about 0.01 and 100 percent by mass, and preferably between 1 and 20 percent by mass.

In one exemplary, non-limiting embodiment, the present invention may comprise:

| Range (Percentage by Mass) | Ingredient |
| --- | --- |
| 35-75% | Vitamin E Succinate |
| 1-30% | Levamisole Hydrochloride (95%) |
| 1-25% | Decoquinate (95%) |
| 1-25% | Diclazuril (95%) |
| 1-20% | Banana Powder |

In another exemplary, non-limiting embodiment, the present invention may comprise:

| Range (Mass in Grams) | Ingredient |
| --- | --- |
| 1-410 g | Vitamin E Succinate |
| 1-410 g | Levamisole Hydrochloride (95%) |
| 1-410 g | Decoquinate (95%) |
| 1-410 g | Diclazuril (95%) |
| 1-410 g | Banana Powder |

In yet another exemplary, non-limiting embodiment, the present invention my comprise:

| Range (Mass in Grams) | Ingredient |
| --- | --- |
| 235-265 g | Vitamin E Succinate |
| 45-75 g | Levamisole Hydrochloride (95%) |
| 25-55 g | Decoquinate (95%) |
| 25-55 g | Diclazuril (95%) |
| 5-35 g | Banana Powder |

In preferred embodiments, the present invention may comprise:

| Mass in Grams | Ingredient |
| --- | --- |
| 250 g | Vitamin E Succinate 1185 IU Powder |
| 60 g | Levamisole Hydrochloride (95%) |
| 40 g | Decoquinate (95%) |
| 40 g | Diclazuril (95%) |
| 20 g | Banana Powder |

Administration:

In some embodiments, the composition—designed to treat horses with EPM by killing the protozoan parasites in the horse's body and by providing agents that limit or remedy the damage caused by the protozoan parasite—is administered to the horse orally. In some embodiments, the composition maybe formulated as a paste. In other embodiments, the composition maybe formulated as a liquid.

In some embodiments, the composition may be administered at a treatment regimen. In some embodiments, the length the regimen may be selected to ensure all EPM causing parasites in the horse's body have been killed. In some embodiments, the regime length may be selected to minimize the risk of relapse. In some embodiments, the regimen may last between 1 and 100 days. In preferred, embodiments, the regimen may last for 30 days.

In some embodiments, the composition is administered multiple times a day. In preferred embodiments, the composition may be administered once a day.

In some embodiments, the composition may be administered as a top dressing to the horse's feed. In some embodiments, the composition may be mixed with the horse's feed. In other embodiments, the composition may be pellets.

What is claimed is:

1. A veterinary composition for the treatment of Equine Protozoal Myeloencephalitis, comprising: therapeutically effective amounts of Vitamin E Succinate, Levamisole Hydrochloride, Decoquinate, Diclazuril, and Banana powder.

2. The veterinary composition of claim 1, wherein the composition is a paste.

3. The veterinary composition of claim 1, wherein the composition is a liquid.

4. The veterinary composition of claim 1, wherein the composition is a pellet.

5. A method for the treatment of Equine Protozoal Myeloencephalitis, comprising the following steps:

providing to a horse a composition, wherein the composition comprises: 250 grams Vitamin E Succinate 1185 IU powder, 60 grams Levamisole Hydrochloride, 40 grams Decoquinate, 40 grams Diclazuril, and 20 grams Banana powder;

apportioning the composition into a dosage, where the dosage equals one thirty-first of the composition by mass; and administering one dosage to the horse daily for thirty-one days.

6. The method of claim 5, wherein the composition is a paste.

7. The method of claim 5, wherein the composition is a liquid.

8. The method of claim 5, wherein the composition is a pellet.

9. The method of claim 5, wherein the composition is administered as a regimen with varying amounts of anti-protozoal drugs administered throughout the regimen.

10. The method of claim 9, wherein the amount of protozoal drug increases near the completion of the regimen.

11. The method of claim 9, wherein the anti-protozoal drug changes during the regimen so that a drug within the composition that takes longer to reach infected site is administered early in the regimen and a drug within the composition that is faster acting is administered later in the regimen.

* * * * *